US012746315B2

(12) United States Patent
Kopperschmidt

(10) Patent No.: US 12,746,315 B2
(45) Date of Patent: Sep. 29, 2026

(54) METHOD FOR CONTROLLING A BLOOD TREATMENT APPARATUS, AND APPARATUSES

(71) Applicant: Fresenius Medical Care Deutschland GmbH, Bad Homburg (DE)

(72) Inventor: Pascal Kopperschmidt, Bad Homburg (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 385 days.

(21) Appl. No.: 18/556,201

(22) PCT Filed: Apr. 21, 2022

(86) PCT No.: PCT/EP2022/060501
§ 371 (c)(1),
(2) Date: Oct. 19, 2023

(87) PCT Pub. No.: WO2022/223669
PCT Pub. Date: Oct. 27, 2022

(65) Prior Publication Data

US 2024/0207494 A1 Jun. 27, 2024

(30) Foreign Application Priority Data

Apr. 22, 2021 (DE) ......................... 102021110331.2

(51) Int. Cl.
*A61M 1/36* (2006.01)
*A61M 1/16* (2006.01)
(Continued)

(52) U.S. Cl.
CPC ........ *A61M 1/3629* (2014.02); *A61M 1/1603* (2014.02); *A61M 60/113* (2021.01);
(Continued)

(58) Field of Classification Search
CPC .. A61M 60/37; A61M 1/3629; A61M 1/3626; A61M 2205/3334; A61M 1/36226
See application file for complete search history.

(56) References Cited

U.S. PATENT DOCUMENTS 5,252,213 A 10/1993 Ahmad et al.
2013/0030344 A1* 1/2013 Gronau ............... A61M 1/3629 137/561 R
(Continued)

FOREIGN PATENT DOCUMENTS

EP 2736561 1/2016
EP 3231466 10/2017
(Continued)

OTHER PUBLICATIONS

International Search Report and Written Opinion in International Appln. No. PCT/EP2022/060501, mailed Aug. 30, 2022, 19 pages.

*Primary Examiner* — Leslie R Deak
(74) *Attorney, Agent, or Firm* — Fish & Richardson P.C.

(57) ABSTRACT

The present disclosure relates to a method for controlling a blood treatment apparatus when air bubbles or air pockets are present in an extracorporeal blood circuit connected to the blood treatment apparatus, which have been detected by an air bubble detector. It further relates to a control device or closed-loop control device and a blood treatment apparatus by which the method described herein is brought into effect, a digital storage medium, a computer program product, and a computer program.

18 Claims, 3 Drawing Sheets

(51) Int. Cl.

| | |
|---|---|
| ***A61M 60/113*** | (2021.01) |
| ***A61M 60/279*** | (2021.01) |
| ***A61M 60/37*** | (2021.01) |

(52) U.S. Cl.

CPC .......... *A61M 60/279* (2021.01); *A61M 60/37* (2021.01); *A61M 1/1656* (2013.01); *A61M 2205/3331* (2013.01)

(56) References Cited

U.S. PATENT DOCUMENTS

| | | | |
|---|---|---|---|
| 2013/0261529 A1 | 10/2013 | O'Mahony | |
| 2017/0296733 A1* | 10/2017 | Riemenschneider | A61M 1/3626 |

FOREIGN PATENT DOCUMENTS

| | | |
|---|---|---|
| EP | 2950834 | 7/2019 |
| JP | 2008-220417 A | 9/2008 |
| JP | 2013-048803 A | 3/2013 |
| JP | 2016-054789 A | 4/2016 |
| JP | 2017-205494 A | 11/2017 |

* cited by examiner

METHOD FOR CONTROLLING A BLOOD TREATMENT APPARATUS, AND APPARATUSES

CROSS-REFERENCE TO RELATED APPLICATIONS

The present application is the national stage entry of International Application No. PCT/EP2022/060501, filed on Apr. 21, 2022, and claims priority to Application No. DE 102021110331.2, filed in the Federal Republic of Germany on Apr. 22, 2021, the disclosures of which are expressly incorporated herein in their entirety by reference thereto.

TECHNICAL FIELD

The present disclosure relates to a method for controlling a blood treatment apparatus as described herein, to a control device or closed-loop control device as described herein, to a blood treatment apparatus as described herein, to a digital storage medium as described herein, to a computer program product as described herein, and to a computer program as described herein.

BACKGROUND

Various types of blood treatment apparatuses are known from practice. They include, for example, apparatuses for hemodialysis, hemofiltration and hemodiafiltration. During the extracorporeal blood treatment, blood flows in an extracorporeal blood circuit through a blood treatment unit. In the apparatuses for hemodialysis, hemofiltration and hemodiafiltration, the blood treatment unit is a dialyzer or filter, which in simple terms is separated by a semi-permeable membrane into a blood chamber and a dialysis liquid chamber. During blood treatment by hemodialysis or hemodiafiltration, the blood flows through the blood chamber, while a dialysis liquid flows through the dialysis liquid chamber.

Air bubbles or microbubbles in extracorporeal circuits downstream of a venous air separation chamber can lead to gas emboli in the patient's body. Emboli can clog vessels and cause ischemia. To prevent gas from entering the patient's vascular system during dialysis, the venous air separation chamber is located in the venous blood tubing system. It partially reduces the flow velocity within the extracorporeal circuit so that gas bubbles can rise against gravity according to Archimedes' principle and be separated through an opening in an upper area of the venous air separation chamber.

In addition, the venous system downstream of the air separation chamber is monitored by an air bubble detector for the presence of air, e.g., in the form of microbubbles, in the extracorporeally flowing blood. If the sensor detects the presence of air, an air bubble alarm is issued, which interrupts the patient's blood treatment. Once the cause of the air bubble alarm has been rectified by the person responsible, blood treatment can be continued.

SUMMARY

It is an aspect of the present disclosure to describe a method for controlling or regulating a blood treatment apparatus after detection of such air bubbles in the extracorporeal blood circuit. Furthermore, a control device or closed-loop control device (in short: control device, which can optionally also regulate) is to be proposed, with which the method can be brought into effect or initiated or carried out. In addition, further apparatuses suitable for carrying out the method, in particular a blood treatment apparatus, a digital storage medium, a computer program product and a computer program, are described herein.

According to the present disclosure, a method for controlling a blood treatment apparatus is thus described, wherein the blood treatment apparatus comprises a blood pump, an air bubble detector and a pump for conveying dialysis liquid and/or dialysate on its hydraulic side. The method is initiated or carried out during an extracorporeal blood treatment session, during which the blood treatment apparatus is connected to an extracorporeal blood circuit and to a blood filter, which in turn comprises a semi-permeable membrane.

Here, e.g., upon detection of air bubbles or air pockets in the extracorporeal blood circuit, or, e.g., upon an air bubble alarm, the method encompasses stopping the blood pump or reducing its conveying rate, at which it was conveying immediately before the detection of air and generating a negative transmembrane pressure across the semi-permeable membrane of the blood filter.

This negative transmembrane pressure can be achieved by appropriately controlling the pump on the hydraulic side while the blood pump is stopped, or its conveying rate is reduced.

The transmembrane pressure can be measured, or its existence detected directly or indirectly in a variety of ways.

Detection of air bubbles or air pockets in the extracorporeal blood circuit can be accomplished using the air bubble detector. The air bubble detector may alternatively or additionally be suitable or configured to trigger an air bubble alarm (alternatively: gas alarm) as a consequence of the detection of gas, air or air bubbles, the alarm in turn leads to the method described herein being initiated or carried out.

Air bubbles or air pockets can be detected, e.g., by an air bubble alarm, by meeting conditions which trigger an air bubble alarm or are sufficient to trigger an air bubble alarm.

According to the present disclosure, a control device or closed-loop control device is further proposed configured to initiate, carry out, control and/or regulate the method described herein, in particular automatically, in interaction with a blood treatment apparatus or its devices or apparatuses, in particular as disclosed herein.

An interaction may be or include actuation, control, or regulation. An interaction may be or require a signal connection.

According to the present disclosure, a blood treatment apparatus is further proposed which respectively comprises at least a blood pump, an air bubble detector, a pump for conveying dialysis liquid and/or dialysate and a control device or closed-loop control device, in particular a control device or closed-loop control device as described herein, which in turn is configured to initiate a method as described herein to be carried out, or is respectively connected to such apparatuses and devices.

For each of the features of the method mentioned herein, the blood treatment apparatus described herein may have a correspondingly suitable and/or configured device or apparatus, such as a pressure measuring device for measuring pressure or the like, etc., or may be connected to such devices or apparatuses.

A digital, particularly non-volatile storage medium, (here also referred to as a carrier), particularly in the form of a diskette, RAM, ROM, CD, hard disk, DVD, USB stick, Flashcard, SD-card or EPROM, particularly with electronically or optically readable control signals, can be configured so that a conventional control device is configured to be a control device or closed-loop control device described herein, by which the herein described method can be initiated or carried out. Alternatively or additionally, the digital storage medium may be configured to configure a blood treatment apparatus into a blood treatment apparatus as described herein, by which the method described herein may be brought into effect or executed.

In this, all or some of the machine-induced method can be initiated.

A computer program product as described herein comprises a volatile or transient program code or one stored on a machine readable carrier through which a control device may be configured into control device or closed-loop control device via which the herein described method can be initiated or carried out. Alternatively, or additionally, via the computer program product a blood treatment apparatus can be configured in such a way that the method described herein may be brought into effect or executed.

In doing so, all, some or a portion of the machine-induced of this method can be initiated.

The term "machine readable carrier" as is as used herein, refers in certain embodiments of the present disclosure to a carrier, which contains data or information interpretable by software and/or hardware. The carrier may be a data carrier, such as a diskette, a CD, DVD, a USB stick, a flashcard, an SD card, an EPROM or the like.

A computer program as described herein comprises a program code by which a control device or closed-loop control device or a blood treatment apparatus is configured in such a way that the method described herein can be initiated or carried out.

In doing so, all or some of the machine-induced method can be initiated.

A computer program product, for example, can be understood as a computer program stored on a carrier, an embedded system being a comprehensive system with a computer program (e.g., an electronic device with a computer program), a network of computer implemented computer programs (e.g., client/server-system, cloud computing system etc.), or a computer on which a computer program is loaded, runs, is stored, is executed or developed.

According to the present disclosure, a computer program can be understood to mean, for example, a physical, marketable software product which comprises a program.

In all of the statements made herein, the use of the expression "may be" or "may have" and so on, is to be understood synonymously with "preferably is" or "preferably has" and so on respectively and is intended to illustrate an embodiment according to the present disclosure.

Whenever numerical words are mentioned herein, the person skilled in the art shall recognize or understand them as indications of a numerical lower limit. Unless it leads the person skilled in the art to an evident contradiction, the person skilled in the art shall comprehend the specification for example of "one" (also "a/an") as encompassing "at least one". This understanding is also equally encompassed by the present disclosure as the interpretation that a numeric word, for example, "one" (also "a/an") may alternatively mean "exactly one", wherever this is evidently technically possible for the person skilled in the art. Both understandings are encompassed by the present disclosure and apply herein to all used numerical words.

Whenever the term "programmed" or "configured" is mentioned herein, it is also disclosed that these terms are interchangeable with one another.

When reference is made herein to a venous air separation chamber or, for short, an air separation chamber, it may also be a venous blood chamber, a venous bubble chamber, or a venous drip chamber.

Whenever an embodiment is mentioned herein, it represents an exemplary embodiment according to the present disclosure.

When it is disclosed herein that the subject-matter according to the present disclosure comprises one or several features in a certain embodiment, it is also respectively disclosed herein that the subject-matter according to the present disclosure does, in other embodiments, likewise according to the present disclosure, explicitly not comprise this or these features, for example, in the sense of a disclaimer. Therefore, for every embodiment mentioned herein it applies that the converse embodiment, e.g. formulated as negation, is also disclosed.

Embodiments according to the present disclosure may comprise one or more of the aforementioned and/or following features in any technically possible combination.

In some embodiments of the method described herein, generating a negative transmembrane pressure across the semi-permeable membrane is performed with the venous tubing clamp fully or partially closed.

In several embodiments, the method comprises opening the venous tubing clamp when a negative transmembrane pressure has already been generated or is present while maintaining a negative transmembrane pressure.

Due to the negative transmembrane pressure, a (transmembrane) plasma water transfer takes place via the semi-permeable membrane and the blood in the dialyzer is hemoconcentrated. Hereby, the volume of liquid pumped into the hydraulic system or shifted from the extracorporeal blood circuit via the semi-permeable membrane to the hydraulic side due to the pressure difference is replaced by blood, which is made to flow in the opposite direction (herein also: retrograde) to its usual direction of flow within the blood circuit via the venous part of the tubing system from the latter and from the patient's vascular system due to the hemoconcentration and the negative pressure. The air bubbles or air pockets (e.g., gas bubbles and microbubbles) in the line are thereby retrogradely conveyed back into the venous air separation chamber and separated there, mostly to the environment.

In some embodiments of the method, the venous tubing clamp is opened when a pressure sensor of the blood treatment apparatus detects that a negative minimum transmembrane pressure has been reached.

In several embodiments, a negative transmembrane pressure is generated by the pump on the hydraulic side of the blood treatment apparatus while an optional substitute pump of the blood treatment apparatus is stopped or is not conveying.

In some embodiments of the method, generating or maintaining the negative transmembrane pressure is terminated once a negative transmembrane pressure of about 300 mmHg to −500 mmHg is reached, or when a volume of at least 30 to 60 ml of blood has been conveyed past the air bubble detector towards the venous air separation chamber by the generated transmembrane pressure.

In some embodiments, conveying by the pump on the hydraulic side of the blood treatment apparatus in order to generate a negative transmembrane pressure is terminated after the air bubble detector no longer detects air bubbles or air pockets and/or there is no longer an air bubble alarm and/or at least 30 to 60 ml of blood has been retrogradely conveyed.

In several embodiments, the pump for conveying dialysis liquid and/or dialysate is an optionally provided ultrafiltration pump.

In some embodiments, the blood treatment apparatus according to the present disclosure is connected to an extracorporeal blood circuit and a blood filter, wherein the blood filter comprises a semi-permeable membrane.

In several embodiments, the extracorporeal blood circuit is a blood tubing set and/or a blood cassette or comprises a blood tubing set and/or a blood cassette.

In some embodiments of the blood treatment apparatus, the pump for conveying dialysis liquid and/or dialysate is an ultrafiltration pump.

In several embodiments, the blood treatment apparatus is embodied as a hemodialysis device, a hemofiltration device, a hemodiafiltration device, or a device for performing a separation procedure.

In some embodiments of the method, this encompasses determining whether the generated negative transmembrane pressure or its absolute value is within predetermined limits, exceeds or falls below a threshold, exceeds a minimum value, and/or does not exceed a maximum value. This can be done on the basis of at least one criterion (threshold, range, maximum value, etc.), which can be stored, for example, in a memory device, such as of the blood treatment apparatus.

In some embodiments, the method comprises emitting or outputting an audible and/or optical or otherwise signal-linked air bubble alarm only if, during or after the course of the method described herein, a state still or once again exists which would already have led to an air bubble alarm for the person responsible and/or the blood treatment apparatus before the start of the method described herein. It can thus be provided that the user is only informed optically and/or acoustically of the presence of an air bubble alarm and/or that the blood treatment is only automatically interrupted if, after air bubbles have been detected, the removal of the detected air by the method described herein.

In some embodiments, the pump is a positive displacement pump, particularly a diaphragm pump, eccentric diaphragm pump, peristaltic pump, roller pump, or piston pump.

When reference is made herein to a signal connection or communication connection between two components, this may be understood to mean a connection that exists in use.

In several embodiments, the extracorporeal blood circuit does not comprise a venous air separation chamber which stands upside down or inverted, or in which a narrower end of the air separation chamber (or the end having a smaller diameter or cross-sectional area) is higher than a wider end thereof (or the end having a larger diameter or a larger cross-sectional area).

In some embodiments, the negative transmembrane pressure is not applied in order to remove air bubbles directly from the air separation chamber, and thus from the extracorporeal blood circuit, bypassing the blood filter.

In several embodiments, the method is not a method for draining a device for an extracorporeal blood treatment.

In some embodiments, the negative transmembrane pressure is applied while the blood pump is stopped and/or not conveying.

Through some embodiments, one or more of the advantages mentioned herein can be achieved, which include the following:

Through the method described herein, a procedure requiring considerable effort on the part of the user can be advantageously avoided. In a conventional case, the user would have to venously disconnect the patient, which involves a hygienically critical disconnection of at least one tubing segment filled with whole blood, and then connect the venous tubing system e.g. to a saline bag, in order to pump the blood volume of the venous line, in which the detected air bubbles or air pockets are present, into the saline bag at a low flow rate. In this conventional method, if the user recognizes that the line is now gas-free, he reconnects the venous line to the patient and continues the treatment. In clinical practice, there have been cases in which these actions were ignored due to the time-consuming procedure for treating intradialytic air bubble alarms, and there was an accepted risk of gas embolism in the patient. Thus, both the treatment can be simplified, and the patient's safety increased.

A further advantage of the present devices, systems, and methods may be that the patient does not suffer any loss of blood during the method described herein by discarding whole blood, e.g., into the aforementioned saline bag. This also advantageously contributes to patient comfort and patient safety.

Through the present method, a fully automated and hygienic method for treating air bubble alarms in the venous line with induced separation of the microbubbles can be provided. This can advantageously help to reduce personnel effort and increase patient safety.

BRIEF DESCRIPTION OF THE DRAWINGS

In the following, the present systems, devices, and methods are described based on the preferred embodiments thereof with reference to the attached drawing. The method and the blood treatment apparatus are described using the example of a hemodialysis device. However, the method described herein can also be used in the same way for other blood treatment apparatuses, for example a hemodiafiltration device. In the figures.

DETAILED DESCRIPTION

Figure 1:
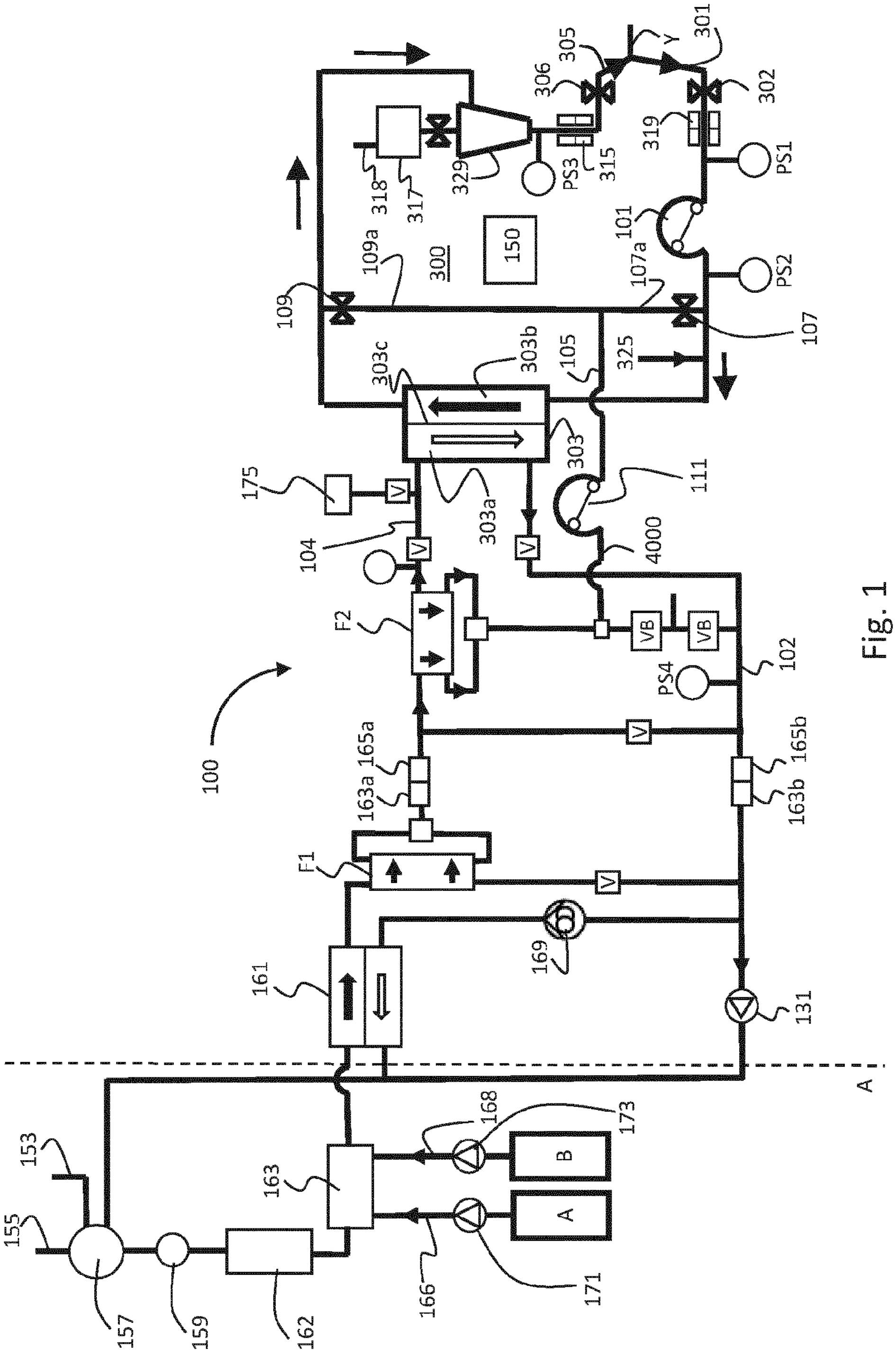
FIG. 1 shows schematically simplified a fluid line structure of a blood treatment apparatus in a first embodiment.

FIG. 1 shows schematically simplified a fluid line structure of a blood treatment apparatus 100 in a first embodiment.

The blood treatment apparatus 100 is connected to an extracorporeal blood circuit 300, which can be connected to the vascular system of the patient, not shown, for a treatment using double-needle access, or via single-needle access using, for example, an additional Y-connector (reference numeral Y) as shown in FIG. 1. The blood circuit 300 may be present, optionally in sections thereof, in or on a blood cassette.

Pumps, actuators and/or valves in the area of the blood circuit 300 are connected with the blood treatment apparatus 100 or to a control device or closed-loop control device 150, for example, encompassed by it.

The blood circuit 300 comprises (or is connected to) an arterial tubing clamp or patient tubing clamp 302 as a first tubing clamp and an arterial connection needle of an arterial section or an arterial patient line, an arterial line section, a blood return line, or first line 301. The blood circuit 300 further comprises (or is connected to) a venous patient tubing clamp 306 as a second tubing clamp and a venous connection needle of a venous section, a venous patient line, a venous line section, a blood return line, or second line 305.

A blood pump 101 is provided in or at the first line 301, a substitute fluid pump 111 is connected to a dialysis liquid inlet line 104 for conveying fresh dialysis liquid, which is filtered in a further filter stage (F2) (substitute fluid). A substitute fluid line 105 may be fluidically connected to the inlet line 104. Using the substitute fluid pump 111, substitute fluid may be introduced by pre-dilution, via a pre-dilution valve 107, or by post-dilution, via a post-dilution valve 109, via associated lines 107*a* or 109*a* into line sections, for example into the arterial line section 301 or into the venous line section 305 (here between a blood chamber 303*b* of a blood filter 303 and a venous air separation chamber or venous blood chamber 329 of the blood circuit 300).

The blood filter 303 comprises the blood chamber 303*b* connected to the arterial line section 301 and to the venous line section 305. A dialysis liquid chamber 303*a* of the blood filter 303 is connected to the dialysis liquid inlet line 104 which leads to the dialysis liquid chamber 303*a* and to a dialysate outlet line 102 which leads away from the dialysis liquid chamber 303*a* whose outlet line 102 conveys dialysate, i.e., used dialysis liquid. For this purpose, suitable connectors are used on the dialysis liquid inlet line 104 or on the dialysate outlet line 102 on the one hand and on the dialysate ports on the other hand, which can be connected to one another, in particular in a detachable manner.

Dialysis liquid chamber 303*a* and blood chamber 303*b* are separated from each other by a mostly semi-permeable membrane 303*c*. It represents the partition between the blood side with the extracorporeal blood circuit 300 and the machine side with the dialysis liquid or dialysate circuit, which is shown in FIG. 1 to the left of the membrane 303*c*.

The arrangement of FIG. 1 comprises an air bubble detector 315 for detecting air and/or blood, preferably in the venous line section 305, e.g., at the location shown.

The arrangement in FIG. 1 optionally further comprises one or two pressure sensors PS1 (upstream of the blood pump 101) and PS2 (downstream of the blood pump 101, it measures the pressure upstream of the blood filter 303 ("pre-hemofilter")) at the points shown in FIG. 1. Further pressure sensors may be provided, e.g., the pressure sensor PS3 downstream of venous air separation chamber 329.

An optional single-needle chamber 317 is used in FIG. 1 as a buffer and/or compensating reservoir in a single-needle method in which the patient is connected to the extracorporeal blood circuit 300 using only one of the two blood lines 301, 305.

The arrangement of FIG. 1 also comprises an optional detector 319 for detecting air bubbles and/or blood.

An addition site 325 for Heparin may optionally be provided.

On the left in FIG. 1, is shown an optional mixing device 163, which provides a predetermined mixture for the respective solution from the containers A (for A-concentrate via concentrate supply 166) and B (for B-concentrate via concentrate supply 168) for use by the blood treatment apparatus 100. The solution contains water from a water source 155 (on-line, e.g., as reverse osmosis water or from bags) which is heated, for example, in an optional heating device 162.

A pump 171, which can be referred to as a concentrate pump or a sodium pump, may be fluidically connected to the mixing device 163 and a source of sodium, for example the container A, and/or conveys out of it, when provided. An optional pump 173, associated with container B, e.g., for bicarbonate, can also be seen.

Furthermore, FIG. 1 shows a waste outlet 153 for the effluent. An optional heat exchanger 157 and a first flow pump 159, which is suitable for de-gassing, complete the arrangement shown.

The optional pressure sensor PS4 downstream of the blood filter 303 on the water side, but preferably upstream the ultrafiltration pump 131 in the dialysate outlet line 102 may be provided for measuring the filtrate pressure or membrane pressure of the blood filter 303.

Blood that leaves the blood filter 303 flows through a venous air separation chamber 329, which may comprise a de-aeration device 318 and may be in fluid communication with the pressure sensor PS3.

The exemplary arrangement shown in FIG. 1 comprises the control device or closed-loop control device 150. It may be in a wired or wireless signal connection with any of the components mentioned herein—especially or in particular with the blood pump 101—to control or regulate the blood treatment apparatus 100.

By using the optional device for on-line mixing of the dialysis liquid, a variation of its sodium content, controlled by the control device or closed-loop control device 150, is possible within certain limits. For this purpose, in particular the measurement values determined by the conductivity sensors 163*a*, 163*b* may be taken into account. Should an adjustment of the sodium content of the dialysis liquid (sodium concentration) or of the substitute fluid turn out to be necessary or desired, this can be done by adjusting the conveying rate of the sodium pump 171.

Furthermore, the blood treatment apparatus 100 comprises devices for conveying fresh dialysis liquid as well as dialysate on the so-called hydraulic side of the blood treatment apparatus 100.

A first valve may be provided between the first flow pump 159 and the blood filter 303, which opens or closes the inlet to the blood filter 303 on the inlet side. A second, optional flow pump 169 is provided, for example, downstream of the blood filter 303, which conveys dialysate to the waste outlet 153. A second valve can be provided between the blood filter 303 and the second flow pump 169, which opens or closes the outlet on the outlet side.

Furthermore, the blood treatment apparatus 100 optionally comprises a device 161 for balancing the flow flowing into and out of the dialyzer 303 on the machine side. The device 161 for balancing is preferably arranged in a line section between the first flow pump 159 and the second flow pump 169.

The blood treatment apparatus 100 further comprises devices, such as the ultrafiltration pump 131, for the precise removal of a volume of liquid from the balanced circuit, as predetermined by the user and/or by the control device or closed-loop control device 150.

Sensors such as the optional conductivity sensors 163*a*, 163*b* serve to determine the conductivity, which in some embodiments is temperature-compensated, as well as the liquid flow upstream and downstream of the dialyzer 303.

Temperature sensors 165*a*, 165*b* may be provided as one or a plurality thereof. Temperature values supplied by them may be used, according to the present disclosure, to determine a temperature-compensated conductivity.

An optional source of compressed air 175, for example in the form of a compressor, may be provided upstream of the blood filter 303 on the machine side.

A leakage sensor 167 is optionally provided. Alternatively, it may also be provided at a different location.

Further flow pumps in addition to or alternatively to, e.g., the one with the reference numeral 169 may also be provided.

A number of optional valves are each denoted with V in FIG. 1. By-pass valves are denoted with VB.

Based on the measurement values of the above-mentioned, optional sensors, the control device or closed-loop control device 150 determines in some embodiments the electrolyte balance and/or fluid balance.

Filters F1 and F2 can be provided connected in series.

Even when using non-pure water, the filter F1 exemplarily serves herein to generate sufficiently pure dialysis liquid by the mixing device 163, which then flows through the blood filter 303, e.g., using the countercurrent principle.

The filter F2 exemplarily serves herein to generate sterile or sufficiently filtered substitute fluid from the sufficiently pure dialysis liquid leaving the first filter F1, by filtering, e.g., pyrogenic substances. This substitute fluid may then be safely added to the extracorporeally flowing blood of the patient and thus ultimately to the patient's body.

The blood treatment apparatus 100 shown in FIG. 1 may be a hemofiltration apparatus, a hemodiafiltration apparatus, or a hemodialysis apparatus.

The present disclosure is not limited to the embodiment described above, which is for illustrative purposes only.

The arrows and arrowheads shown in FIG. 1 generally indicate the direction of flow in each case.

The arterial line section 301 and the venous line section 305 may be part of or form a blood tubing set.

Figure 2:
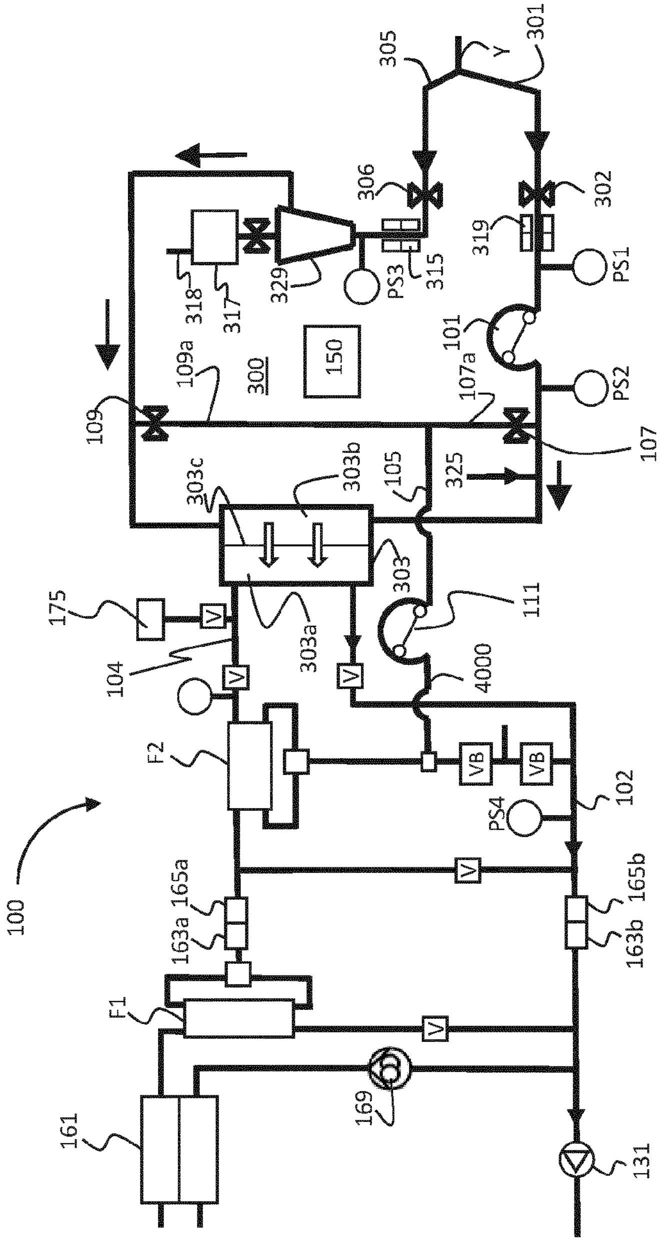
FIG. 2 shows schematically simplified a part of the blood treatment apparatus of FIG. 1 during the method described herein.

FIG. 2 shows schematically simplified a part of the blood treatment apparatus 100 of FIG. 1, namely the part to the right of the dashed line A, during the method described herein.

To avoid repetition, reference is made to the description of FIG. 1.

Figure 3:
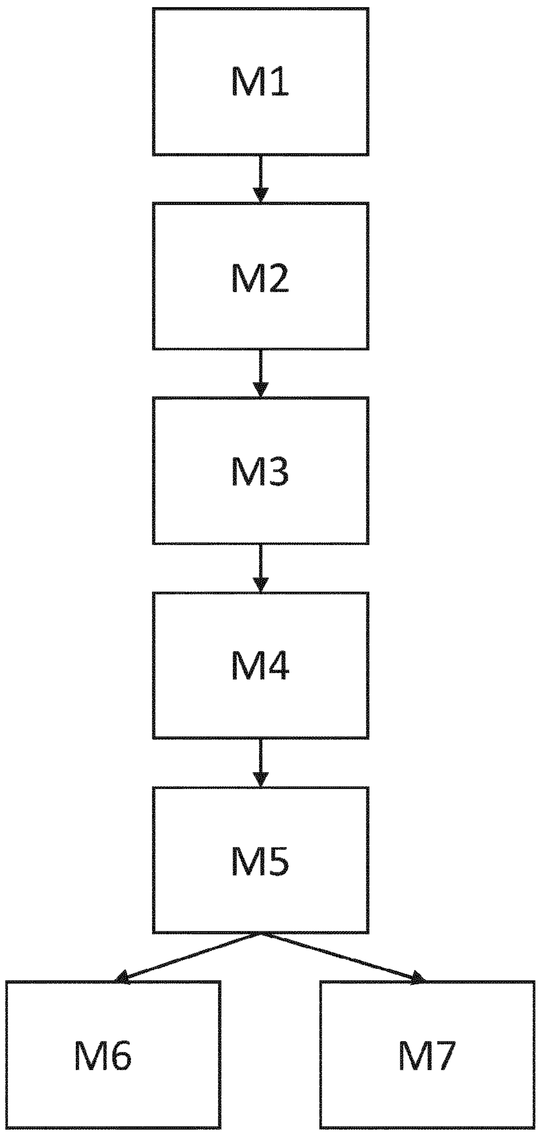
FIG. 3 shows schematically simplified the course of the method described herein.

The method, described in more detail in FIG. 3, results in flow reversal in the venous line section 305, as indicated by the reverse direction of the arrows and arrowheads compared to FIG. 1, in order to prevent or noticeably reduce the flow between the patient and the venous tubing clamp 306, and for the transfer of fluid from the blood chamber 303*b* to the dialysis liquid chamber 303*a*, as also indicated via arrows.

FIG. 3 schematically shows the course of the method described herein.

The blood treatment apparatus 100, which is to be controlled via the method, comprises a blood pump 101, an air bubble detector 315 and a pump for conveying dialysis liquid and/or dialysate on the hydraulic side of the blood treatment apparatus 100 (see FIG. 1 and FIG. 2). The method is to be executed during an extracorporeal blood treatment session, i.e., intradialytically. Meanwhile, the blood treatment apparatus 100 is connected to an extracorporeal blood circuit 300 and to a blood filter 303. The blood filter 303 in turn comprises a semi-permeable membrane 303*c*.

In using the reference numerals for the components of the blood treatment apparatus, reference is made to the reference numerals in FIG. 1 and FIG. 2.

The method optionally comprises as M1 detecting air bubbles or air pockets in the extracorporeal blood circuit 300 or detecting an air bubble alarm. The air bubbles or air pockets may be detected using the air bubble detector 315. Alternatively, or additionally, the latter may be suitably configured to trigger an air or gas bubble alarm as a result of the detection of air bubbles.

In certain embodiments, M1 is not part of the method, but is considered a prerequisite for carrying out the same.

Method M2 represents a stopping of the blood pump 101 or, alternatively, a reduction of its conveying rate in relation to its conveying rate provided immediately before air bubbles were detected.

Optional M3 represents a complete or partial closing of the venous tubing clamp 306.

A generating of a negative transmembrane pressure $P_{TM}$ across the semi-permeable membrane 303*c* by a corresponding activation of the pump, here the ultrafiltration pump 131, on the hydraulic side of the blood treatment apparatus while the blood pump 101 is stopped or its conveying rate is reduced is represented by M4.

M5 represents opening the venous tubing clamp 306 when a negative transmembrane pressure $P_{TM}$ has already been generated while maintaining a negative transmembrane pressure $P_{TM}$ or when the transmembrane pressure $P_{TM}$ is negative.

In several embodiments, the venous tubing clamp 306 is then opened when a negative minimum transmembrane pressure $P_{TM\_min}$ is detected, for example, by at least one pressure sensor PS4 of the blood treatment apparatus 100.

In some embodiments, the pressure sensor PS3 (venous sensor) or the pressure sensor PS2 will be used to assess the pressure situation. In these as well as any other embodiments, the determined pressures may be monitored to detect a pressure drop and open the venous tubing clamp 306 accordingly. Experience has shown that the operating pressure during treatment is mostly about 320 mmHg for PS3, and about 300 mmHg for PS2.

Due to the negative transmembrane pressure, a (transmembrane) plasma water transfer takes place via the membrane and the blood hemoconcentrates in the dialyzer. Hereby, the volume pumped into the hydraulic system is replaced by the blood flowing out of the patient via the venous tubing system in the opposite direction to the usual flow direction. The air bubbles or air pockets (gas bubbles and microbubbles) located in the tubing are returned to the venous air separation chamber where they are separated, for example, into the environment.

In certain embodiments, a negative transmembrane pressure $P_{TM}$ is generated by the pump while an optional substitute pump 111 of the blood treatment apparatus 100 is stopped or does not pump.

M6 represents stopping the generating or maintaining of the negative transmembrane pressure $P_{TM}$ once a predetermined negative transmembrane pressure $P_{TM}$, which is, for example, in the range between 300 mmHg and 500 mmHg, has been reached or a volume of at least 30 to 60 ml of blood has been conveyed towards an arterial needle or a venous air separation chamber 329 via, or due to, the generated transmembrane pressure $P_{TM}$.

Alternatively, in M7, the conveying via the pump in order to generate a negative transmembrane pressure $P_{TM}$ is terminated after the air bubble detector 315 no longer detects any air bubbles or air pockets and/or there is no longer an air bubble alarm.

The pump for conveying dialysis liquid and/or dialysate on the hydraulic side of the blood treatment apparatus 100 can be, for example, the ultrafiltration pump 131.

LIST OF REFERENCE NUMERALS

100 blood treatment apparatus
101 blood pump
102 dialysate outlet line
104 dialysis liquid inlet line
105 substitute fluid line

107 pre-dilution valve
107*a* line associated with the pre-dilution valve
109 post-dilution valve
109*a* line associated with the post-dilution valve
111 substitute fluid pump
131 ultrafiltration pump
150 control device
153 waste outlet
155 water source
157 heat exchanger
159 first flow pump
161 balancing device
162 heating device
163 mixing device
163*a* conductivity sensor
163*b* conductivity sensor
165*a* temperature sensor
165*b* temperature sensor
166 concentrate supply
167 leakage sensor
168 concentrate supply
169 second flow pump
171 pump; sodium pump
173 pump; bicarbonate pump
175 compressed air source; compressor
300 extracorporeal blood circuit
301 first line (arterial line section)
302 (first) tubing clamp; arterial tubing clamp
303 blood filter or dialyzer
303*a* dialysis liquid chamber
303*b* blood chamber
303*c* semi-permeable membrane
305 second line (venous line section)
306 (second) tubing clamp; venous tubing clamp
315 air bubble detector
317 single-needle-chamber
318 de-aeration device
319 detector
325 addition point for Heparin
329 venous air separation chamber
F1 filter
F2 filter
A holder
B holder
K compressed air source, compressor
PS1 arterial pressure sensor (optional)
PS2 arterial pressure sensor (optional)
PS3 pressure sensor (optional)
PS4 pressure sensor for measuring the filtrate pressure
$P_{TM}$ negative transmembrane pressure
$P_{TM\_min}$ minimal negative transmembrane pressure
M1 to M7 method features
V valves
VB bypass valves
Y Y-connector

The invention claimed is:

1. A method for controlling a blood treatment apparatus, which comprises a blood pump, an air bubble detector and a pump for conveying dialysis liquid and/or dialysate, during an extracorporeal blood treatment session, during which the blood treatment apparatus is connected to a blood filter having a semi-permeable membrane and to an extracorporeal blood circuit, the extracorporeal blood circuit being connected to a patient, wherein the method comprises:

detecting air bubbles in the extracorporeal blood circuit with the air bubble detector;

after the detection of air bubbles, stopping the blood pump or reducing the conveying rate of the blood pump, wherein the conveying rate is provided immediately before the detection of air bubbles; and generating a negative transmembrane pressure across the semi-permeable membrane by activating the pump for conveying dialysis liquid and/or dialysate while the blood pump is stopped or the conveying rate is reduced, thereby removing blood from the patient.

2. The method according to claim 1, wherein the generation of a negative transmembrane pressure across the semi-permeable membrane takes place with a venous tubing clamp completely or partially closed.

3. The method according to claim 2, further comprising opening the venous tubing clamp when negative transmembrane pressure has already been generated and while maintaining the negative transmembrane pressure.

4. The method according to claim 3, wherein the venous tubing clamp is opened when a pressure sensor of the blood treatment apparatus determines that a negative minimum transmembrane pressure has been achieved.

5. The method according to claim 1, wherein the negative transmembrane pressure is generated while a substitute fluid pump of the blood treatment apparatus is stopped or does not convey.

6. The method according to claim 1, wherein the generating or maintaining of the negative transmembrane pressure is terminated as soon as a predetermined negative transmembrane pressure has been reached or a volume of at least 30 to 60 ml or more of blood has been conveyed in a direction of an arterial connection needle or a venous air separation chamber via or due to the generated transmembrane pressure.

7. The method according to claim 6, wherein the predetermined negative transmembrane pressure is between −300 mmHg and −500 mmHg.

8. The method according to claim 1, wherein the conveying by the pump for conveying dialysis liquid and/or dialysate in order to generate a negative transmembrane pressure is terminated after the air bubble detector does not detect any air bubbles or air pockets, and/or an air bubble alarm or criteria predetermined for the conveying the pump for conveying dialysis liquid and/or dialysate are no longer present.

9. The method according to claim 1, wherein the pump for conveying dialysis liquid and/or dialysate is an ultrafiltration pump.

10. A control device or closed-loop control device configured to initiate or carry out the method according to claim 1 in interaction with the blood treatment apparatus.

11. A blood treatment apparatus comprising or connected to:

a blood pump;

an air bubble detector;

a pump for conveying dialysis liquid and/or dialysate; and a control device or closed-loop control device according to claim 10.

12. The blood treatment apparatus according to claim 11, connected to an extracorporeal blood circuit and to a blood filter, the filter having a semi-permeable membrane.

13. The blood treatment apparatus according to claim 12, wherein the extracorporeal blood circuit is or comprises a blood tubing set and/or a blood cassette.

14. The blood treatment apparatus according to claim 11, wherein the pump for conveying dialysis liquid and/or dialysate is an ultrafiltration pump.

15. The blood treatment apparatus according to claim 11, embodied as a hemodialysis apparatus, hemofiltration apparatus, hemodiafiltration apparatus, or as an apparatus for carrying out a separation method.

16. A digital storage medium, in the form of a floppy disk, CD or DVD or EPROM, with electronically readable control signals, configured in order to configure a control device or closed-loop control device into a control device or closed-loop control device according claim 10.

17. A computer program product with a program code stored on a machine-readable carrier in order to configure a control device or closed-loop control device into a control device or closed-loop control device according to claim 10.

18. A computer program with a program code in order to configure a control device or closed-loop control device into a control device or closed-loop control device according to claim 10.

* * * * *